(12) United States Patent
Guillemet et al.

(10) Patent No.: US 6,270,792 B1
(45) Date of Patent: Aug. 7, 2001

(54) STERILE NONSTICK COMPRESS

(75) Inventors: Alain Guillemet, Fontaine-les-Dijon; Michel Fasne, Talant, both of (FR)

(73) Assignee: Laboratories d'Hygiene et de Dietique (FR)

( * ) Notice: Subject to any disclaimer, the term of this patent is extended or adjusted under 35 U.S.C. 154(b) by 0 days.

(21) Appl. No.: 09/399,231

(22) Filed: Sep. 17, 1999

(30) Foreign Application Priority Data

Sep. 18, 1998 (FR) .................................................. 98 11676

(51) Int. Cl.[7] .......................... A61F 13/00; A61L 15/00; A61L 15/16
(52) U.S. Cl. .......................... 424/443; 424/443; 424/445; 424/446; 424/447; 604/304
(58) Field of Search .................................... 424/443, 445, 424/446, 447; 604/304

(56) References Cited

U.S. PATENT DOCUMENTS 5,389,092 * 2/1995 Guillemet et al. .................... 604/304
5,681,579 * 10/1997 Freeman .............................. 424/448

FOREIGN PATENT DOCUMENTS

| 0261167B1 | 1/1992 | (EP) . | |
|---|---|---|---|
| 0 497 607 | * 8/1992 | (EP) | .............. A61F/13/02 |
| 0521761 | 1/1993 | (EP) . | |
| 0 567 704 | * 11/1993 | (EP) | .............. A61F/13/00 |
| 0420841B1 | 1/1994 | (EP) . | |
| 0521761B1 | 10/1996 | (EP) . | |
| 0497607B1 | 11/1996 | (EP) . | |
| 0567704B1 | 2/1997 | (EP) . | |
| 0617938B1 | 8/1998 | (EP) . | |
| 89/02754 | 4/1989 | (WO) . | |
| WO 89/02754 | * 4/1989 | (WO) | .............. A61L/15/03 |

* cited by examiner

*Primary Examiner*—Thurman K. Page
*Assistant Examiner*—Isis Ghali
(74) *Attorney, Agent, or Firm*—Steinberg & Raskin, P.C.

(57) ABSTRACT

A sterile nonstick compress having an open-mesh flexible fabric, the fabric including yarns which are coated with a cohesive and nonstick gel so as to leave the meshes essentially unobstructed, the gel being formed from a highly plasticized hydrophobic elastomeic matrix having a dispersion of hydrophilic particles of a hydrocolloid.

11 Claims, No Drawings

STERILE NONSTICK COMPRESS

The present invention relates to a sterile nonstick compress intended to be applied directly in contact with a wound.

PRIOR ART

The advantages of a greasy interface put into direct contact with a wound so as to promote healing, while at the same time ensuring separation between said wound and an absorbent compress, have been known for a long time. One of the products frequently used for covering skin wounds is the "Lumière" tulle gras dressing sold by Solvay Pharma. However, this product, formed from a wide-mesh net made of viscose, coated with a grease based on vaseline and Peru balm, has drawbacks such as, for example, frequent adhesion to the wound or the loss of grease on the handling tools or on the wound after the dressing has been removed. There are also other products, sold or described in the literature, capable of fulfilling the same functions as the aforementioned tulle gras dressing. For example, the dressing with the brand name JELONET sold by Smith and Nephew is known, this being a paraffin-impregnated cotton gauze, the dressing with the brand name ADAPTIC (Johnson and Johnson) which is a viscose knit impregnated with an oil-in-water emulsion: these various products behave in a quite similar manner to the abovementioned "Lumière" tulle gras dressing. Also known is the product with the brand name MEPITEL, sold by Mölnlycke, corresponding to Patent EP 261,167, which is an extensible elastic net covered with a hydrophobic silicone gel capable of adhering to dry skin; however, this product remains little used because of the high cost of silicone gels and its strong adhesion. Among the documents published in a similar field, mention may be made of EP 497,607 which recommends the use of a hydrophilic adhesive resin on a net dressing, but, like the previous product, this has a strong adhesion to perilesional skin and may consequently result in painful removal of the dressing. EP 521,761 describes a healing dressing consisting of a continuous layer of a highly plasticized triblock elastomer having a saturated central block, which layer forms an occlusive, nonstick and highly hydrophobic dressing. In a similar field, mention may also be made of EP 567,704 which describes an antiseptic dressing formed from a hydrogel material impregnated into an absorbent layer which swells in the presence of moisture; in this case, it comprises a continuous layer which essentially seems intended for making a dressing on nonexuding and superinfected wounds. In a similar field of application, EP 420,841 describes a dressing, designed to release an active principle, formed from an adhesive strip to which corpuscles are bonded, these consisting of a hydrophobic matrix in which hydrophobic particles containing the active principle are dispersed. EP 752,840 claims a dressing formed from a thermoplastic polymer forming a hydrogel which is impregnated in a fibrous substrate. The polymer capable of forming a hydrogel is obtained by the copolymerization of hydrophobic groups and hydrophilic groups. The product obtained by the copolymerization is impregnated into the yarns of the substrate, which consists of a cotton gauze for example. The product obtained may be regarded as being a polymer having both a hydrophobic nature and a predominant hydrophilic nature, so that the hydrogel is highly absorbent. According to EP 617,938, a dressing is also known which is composed of an occlusive sheet and a discontinuous polymer layer containing a hydrocolloid, the desired aim being to obtain greater absorption and to prevent leaks.

However, these various products are not entirely satisfactory, either because of a high cost, or because of handling difficulties when putting the dressing in position or removing it, or else because the expected result—i.e. uniform and rapid healing of the wound—can only be achieved with very great difficulty.

As to the last point, which is certainly the most important, it is known that the healing of the wound can progress favorably only if the dressing does not adhere to the newly regenerated tissue and only if the exudates are removed, while still leaving the wound wet.

In use, it seems that the known dressings of the tulle gras type usually adhere strongly to the wound, which generally means that the dressing is painful to remove and considerably reduces the speed of healing because of the disturbance caused by the removal of the dressing. Moreover, it has been noticed that if the compress is too hydrophobic, the wound tends to dry out and that, if the compress is completely hydrophilic, the layer in contact with the wound swells, closes off any passages made in the contact layer and may cause maceration of the wound.

In the medical field, it therefore seems to be desirable to have a wound-contacting compress which is perfectly non-stick to regenerated tissue and which maintains optimum moisture conditions favorable to healing, whilst avoiding the risk of maceration.

SUBJECT OF THE INVENTION

The invention aims to provide a technical solution to the problem mentioned, by means of a sterile nonstick compress of the type comprising an open-mesh flexible fabric, said fabric comprising yarns which are coated with a cohesive and nonstick gel so as to leave the meshes essentially unobstructed, in which compress the gel is formed from a highly plasticized hydrophobic elastomeric matrix containing, in a small amount, a dispersion of hydrophilic particles of a hydrocolloid.

According to one of the preferred embodiments of the invention, the material forming the fabric is a synthetic fiber having long or continuous filaments and, more favorably, is a polyester yarn.

According to another preferred embodiment of the invention, the hydrophobic matrix is based on a high-molecular-weight triblock elastomer of the S-EB-S type.

According to yet another preferred embodiment of the invention, the elastomer is plasticized using a mixture of vaseline and paraffin oil in a proportion of at least 65% by weight of the gel.

According to another preferred embodiment of the invention, the hydrocolloid dispersed in the gel is a sodium salt of carboxymethylcellulose.

DETAILED DESCRIPTION

It has been noticed in fact that the addition of a small amount of hydrocolloid dispersed in a cohesive and elastic, hydrophobic elastomeric matrix gives the surface of the gel obtained a hydrophilic nature, this being combined with the hydrophobic nature of the matrix highly plasticized by an oil, but does not induce water absorbency. These hydrophobic and hydrophilic properties, comparable to an amphiphilic character of the surface of the gel which comes into direct contact with the wound, are translated into a result extremely favorable to the wound-healing process—an optimum degree of moisture maintained on the surface and the presence of grease insulating the structure of the dressing cause more rapid healing and the complete absence of adhesion of the compress to the wound.

The use of a cohesive and elastic gel, stable in a wet environment, allows the yarns of the fabric to be properly trapped, these yarns remaining perfectly isolated from the wound as long as the compress remains in place; there is therefore no risk at any time of establishing direct contact between yarn and regenerated tissue, something which could cause yarn to be introduced into the scar, with, as a consequence, painful destruction of the tissue when removing the dressing. The addition of a large amount of oily plasticizer allows the hydrophobic matrix to be given very pronounced elasticity and flexibility properties; thus, a very compliant compress is obtained which adapts well to the surface to be protected and which at no time deteriorates because of strong cohesion and elasticity of the matrix greater than the elasticity of the coated yarn. Moreover, the oily plasticizer, preferably obtained from a mixture of mineral oil and officinal vaseline, gives a greasy appearance and nonstick properties to the surface of the compress; this results in very limited direct contact between the elastomer and the wound, essentially all contact taking place via the oily compounds, these being better tolerated than elastomeric polymers by the living tissue of the wound.

The hydrocolloid dispersed in the gel in a relatively small amount makes it possible to obtain a slightly hydrophilic nature, sufficient to maintain the wet environment favorable to healing but insufficient to make the gel capable of absorbing a great deal of water. In fact, this absorbency is not desirable since it would result in the gel swelling, which would cause progressive obstruction of the apertures left in the structure of the compress. The compress would then become occlusive, thus eliminating the possibility of getting rid of the exudates, leading to a risk of maceration.

According to one of the characteristics of the invention, the healing compress comprises a support formed from a fabric of yarns made of a flexible material which has a very low extensibility and is nonelastic. This support is in the form of a fabric having wide, open meshes and can be obtained by weaving or knitting processes allowing square or polygonal open meshes of uniform size to be formed. In the case of weaving, the meshes may be fixed by means of turning yarns so as to obtain good dimensional stability. The size of the meshes is such that the unit area of the apertures is about 0.5 to 10 mm$^2$, preferably 0.5 to 3 mm$^2$, the open aperture ratio of the fabric (the ratio of the open area to the total area) being about 50 to 90%. The yarn used for manufacturing the fabric is preferably a continuous multifilament yarn which is nonelastic and is not very extensible, the extensibility or elongation being less than 35%. The expression "continuous multifilament yarn" should be understood to mean a yarn formed from one or more long twisted filaments; the choice of long filaments makes it possible to avoid short fibers which run the risk of becoming detached from the support and being dispersed close to the area of contact with the wound. For the same reason, the material of which the yarns are made is preferably of the hydrophobic type and of an artificial or synthetic nature; these constituents, such as polyesters, polyamides and cellulose acetates for example, make it possible to obtain long filaments and yarns having many fewer fibrils than the fibers obtained, for example, from short fibers. The choice of certain synthetic materials, such as polyesters, also gives the possibility of heat-setting the wide-mesh structure of the support. The wide-mesh fabric is preferably made using yarns of the same nature, but it is also possible to use fabrics manufactured, for example, using warp yarns and filling yarns which are different in nature. Finally, another advantage of the nonelastic materials of very low extensibility, such as polyesters, is the easier processing during the process of covering the yarns of the fabric with the gel.

According to another characteristic of the invention, the fabric support is coated with a nonstick gel of greasy appearance so as to leave most of the apertures of said support open; this gel is composed of a hydrophobic triblock thermoplastic elastomer matrix, highly plasticized using an oil or grease which is immiscible with water, and contains a dispersion of hydrocolloid particles. This combination of a hydrophobic elastic flexible matrix and dispersed hydrophilic hydrocolloid particles gives the dressing properties extremely favorable to healing—the hydrophobic matrix gives the compress good physical stability, which can remain in place on the wound for several days without migrating or being dispersed and without adhering to the freshly regenerated tissue, and the hydrophilic component makes it possible to maintain a degree of moisture favorable to the healing process while preventing the wound from drying out and, consequently, either preventing a crust forming or preventing the dressing adhering to the wound.

In practice, a hydrophobic synthetic thermoplastic elastomer of the (styrene-ethylene/butylene-styrene) or (styrene-ethylene/propylene-styrene) triblock type, that is to say formed from the copolymerization of polystyrene-type blocks and polyolefin blocks of the polyethylene-butylene or polyethylene-propylene type, is chosen. In order to obtain a hydrophobic material according to the invention, S-EB-S or S-EP-S type triblock elastomers are chosen which have a moderate or high molecular weight and a Brookfield viscosity of at least 300 cp (measured at 25° C., for a 10% solution in toluene).

The particular choice of this type of elastomer, combined with an oily plasticizer, makes it possible to obtain a highly cohesive and elastic gel of greasy appearance and exhibiting virtually no adhesion (the adhesive strength, measured on a glass plate, is less than 8 g/5 cm).

The hydrophobic thermoplastic elastomer must be plasticized by adding a hydrophobic oily component: to do this, a mineral or vegetable oil is chosen which has both good compatibility with the elastomers described above and a recognized tolerance with respect to skin tissue. It is preferred to use low-viscosity paraffin oils based on paraffinic and naphthenic compounds or mixtures of paraffin oil and officinal vaseline.

Among the products very suitable for plasticizing the elastomer, mention may be made, for example, of the paraffin oils sold under the brand name ONDINA by Shell, more particularly the oil sold under the reference ONDINA 15, which, in combination with a vaseline in accordance with the French Pharmacopeia, makes it possible to obtain one of the preferred formulations of the invention. The triblock-type elastomer must be combined with a plasticizing oil in proportions such that an extensible and elastic hydrophobic gel having an elongation at break of at least 200%, with a spring-back of at least 50%, is obtained. In general, a gel may be obtained which is sufficiently cohesive, very compliant and elastic, by plasticizing 100 parts of elastomer with 1000 to 2000 parts of a low-viscosity oil and 0 to 400 parts of vaseline. A preferred embodiment corresponds to the combination of 100 parts of a high-molecular-weight S-EB-S elastomer, such as, for example, Kraton G 1651 sold by Shell, with 1600 parts of a hydrophobic oily plasticizer composed of 95% low-viscosity paraffin oil free of aromatic derivatives, and 5% vaseline in accordance with the French Pharmacopeia. This example is given by way of indication, it being possible, of course, to obtain a gel according to the invention using different proportions and different materials.

As indicated previously, the addition is made of fine hydrophilic particles of a hydrocolloid dispersed in the hydrophobic matrix described above. The term "hydrocolloid" should be understood to mean here compounds known to those skilled in the art as capable of absorbing water; among these, pectin, alginates and carboxylmethylcellulose may essentially be mentioned, the latter being, in the form of the sodium salt, preferred for carrying out the invention. The hydrocolloid must be in a solid and finely divided form, for example in the form of a powder whose average particle size is less than 100 $\mu$m, and better still less than 50 $\mu$m. The amount of hydrocolloid used in the formulation of the gel depends on the type of hydrocolloid employed. However, it is worth pointing out that a small amount of this compound gives the gel a hydrophilic nature sufficient for maintaining a wet environment favorable to healing, while preventing the wound from drying out, which could result in adhesion of the dressing. If sodium carboxymethylcellulose (SCMC) is used, the addition of only 2 to 3% of SCMC makes it possible to obtain a gel having a surface state which remains slightly wet and slippery in the presence of a wound. Amounts greater than 20% disturb the cohesive nature of the gel, greatly accentuate its hydrophilic nature and do not allow the expected result to be improved, whilst increasing the risk of the matrix swelling and, consequently, the risk of the apertures of the compress becoming obstructed. In practice, the hydrocolloid, in the form of a fine powder, is incorporated in an amount of 3 to 20% (by weight with respect to the weight of the hydrophobic matrix) into the hydrophobic matrix during the high-temperature mixing phase and is thus dispersed homogeneously in the gel. The intimate mixing of the hydrophobic plasticized elastomer forming a matrix in which the hydrocolloid is dispersed makes it possible to obtain the characteristic properties of an amphiphilic gel, which is capable of maintaining a sufficiently wet environment without having the absorbency of compounds with a high loading of hydrocolloids. According to a variant of the process, the hydrophobic gel can be formulated independently without hydrocolloid, coated on the support so as to coat the yarns, and can leave the mesh apertures unobstructed and, while the gel is still hot, the fine hydrocolloid particles are sprayed onto the surface of the gel. According to this variant of the process, an amount of about 0.2 to 0.5% by weight of hydrocolloid is sufficient to obtain a nonstick compress having an amphiphilic nature on the surface and exhibiting satisfactory behavior on a wet wound. This process also makes it possible to produce an asymmetric compress, by spraying the hydrocolloid particles only on that side intended to be exposed to direct contact with the wound—in this way, a compress having a hydrophilic side and a hydrophobic side is obtained.

In practice, and conventionally, the composition also comprises one or more antioxidants or stabilizers such 5as, for example, phenolic compounds sold under the brand name IRGANOX by Ciba-Geigy.

It is also possible to add active principles to the formulation of the gel if it is desired to add a particular therapeutic effect to the healing properties of the compress. To do this, compounds having antiseptic properties may be dispersed in the gel, such compounds being, for example, silver sulfadiazine, antibiotics such as, for example, neomycin or polymyxin, and nonsteroidal or steroidal anti-inflammatories such as, for example, triamcinolone acetonide.

According to one of the preferred embodiments of the invention, a wide-mesh fabric is coated with a gel so as to coat the yarns of the fabric, leaving most of the meshes unobstructed.

As indicated previously, a woven or knitted support is used which has wide rectangular, square or polygonal meshes, the openness of which corresponds to approximately 4 to 20 meshes per cm, the fabric having an open aperture ratio (ratio of the open areas to the total area) of 50 to 90%. The yarn used to obtain the support is preferably a continuous multifilament yarn and, in order to produce the preferred examples of the invention, yarns made of an artificial or synthetic material having a hydrophobic nature and an extensibility of less than 35% are chosen. The nature of the yarn is, for example, a polyester of the polyethylene terephthalate type, a polyamide or a cellulose acetate; it is preferred to use a fabric having heat-set wide meshes made of continuous polyester yarns (TERGAL or polyethylene terephthalate), for example fabrics sold under the name marquisette, having a grammage of approximately 30 to 80 g/m$^2$. These fabrics, virtually inextensible in the warp and filling directions, have the advantage of being more easy to work with than elastic fabrics, and a more uniform coating of the yarns is obtained.

The nonstick gel is preferably obtained by hot mixing without a solvent (so-called hotmelt process), by blending the elastomer with the oily plasticizer and the antioxidants, and then by adding the hydrocolloid as a finely divided powder. If active principles are provided, these may be added to the latter.

The process of coating the fabric with the gel must allow the yarns to be properly trapped in the gel, whilst leaving most of the apertures unobstructed by the gel. Depending on the structure of the support used, the amount of gel employed will vary from about 50 to 300 g/m$^2$, and preferably from 60 to 160 g/m$^2$. On account of the gel components, the coating is carried out hot, without a solvent, using a continuous process in which the web of fabric is directed over a first coating roll covered with a layer of molten gel having a thickness predetermined by a doctor, and then over a second roll which removes the gel lying within the apertures of the meshes. The web thus covered with gel only on the yarns is then cooled in a zone of upwardly blown air so that the gel cannot flow and remains uniformly distributed around the yarns. If necessary, a system producing a laminar stream of air is provided, which system is able both to correct the distribution of the gel around the yarns and to unblock any mesh apertures which would not have been open in the previous step of the process.

According to a variant of this process, the web of fabric is passed through a bath of molten gel at 140–150° C.; the web covered with molten gel is then passed between two fixed rolls pressed against each other with a predetermined gap, so as to remove the excess gel. The amount of gel remaining on the yarns depends essentially on the gap set between the fixed rolls. The covered web is then cooled and treated in a manner similar to the previous process.

Next, the cooled web of nonstick compress is covered with two protective films, for example thin polyester films. Because of the nonstick nature of the web of compress, these films do not require a nonstick treatment and their function is only to facilitate extraction from the main package and to handle it when it is being placed over the wound. Next, the web is cut into individual compresses, of sizes suitable for the use, packaged in sealed sachets and sterilized.

The nonstick compress according to the invention can be used in a manner similar to the currently known interfaces such as, for example, the "Lumière" tulle gras dressing. Conventionally, the compress is placed in direct contact with the wound and can be used as a single layer or as multiple layers; the compliance of the support and of the gel allows the compress to be properly applied over the entire area of the wound, by extending beyond the perimeter as far as the healthy skin. Next, the sterile compress is covered with an absorbent pad if the wound is exuding considerably, and the assembly is held in place by an adhesive strip or tape which is fixed to the peripheral regions of healthy skin away from the wound. The dressing thus produced may remain in place for a prolonged period since the highly cohesive gel does not disintegrate and the small amount of hydrocolloids present maintains a degree of moisture on the surface of the wound, sufficient to prevent the latter from drying out. In addition, because of the nonstick nature of the gel used, it is possible, virtually without any risk, to remove the absorbent pad, which does not adhere to the gel, without moving the sterile compress in order to monitor the change in the wound. Although the compress is translucent, thereby allowing the wound to be examined because of its transparency, it may also be necessary to remove this compress in order to make a more precise visual examination or to carry out a direct pharmaceutical treatment of the region in the process of healing; this removal can be done easily without any pain and without damaging the newly regenerated tissue since the gel adheres neither to the surface of the wound nor to the perilesional skin. In addition, because of the high cohesion of the gel in which the yarns of the fabric are trapped and the presence of SCMC which maintains a slightly wet environment, the compress can be removed integrally without leaving particles or grease, as occurs with certain products sold at the present time. Consequently, it is markedly easier to clean the wound. All these advantages, namely excellent cohesion together with nonstickability to wet surfaces and to dry skin, combine to give the best conditions favorable to the wound-healing process. The following illustrative examples enable the scope of the invention to be more fully appreciated, but they must not be regarded as being restrictive.

EXAMPLE 1

The gel is prepared by mixing, at 150° C., 8 kg of paraffin oil (ONDINA 15 sold by Shell), 1 kg (i.e. approximately 5% of the total mass of the gel) of high-molecular-weight S-EB-S elastomer (KRATON G 1651 sold by Shell) and 25 g of antioxidant (IRGANOX 1010). When the mixture is homogeneous, 1 kg (i.e. approximately 5% of the mass of the gel) of vaseline (a grade in accordance with the French Pharmacopeia or Codex) and 7.2 kg (i.e. in total approximately 75% of the mass of the gel) of ONDINA 15 oil are added. After mixing for 30 minutes, the temperature is lowered to 130–135° C. and 3.04 kg (i.e. approximately 15% of the mass of gel) of sodium carboxymethylcellulose (ref. 7H4XF sold by Aqualon) are added. After mixing for 40 minutes, the gel can be used to coat the yarns of the fabric. The fabric used is a heat-set marquisette made of 33 decitex warp and filling yarns of polyester (polyethylene terephthalate), having square meshes of aperture approximately 0.8 to 1 mm$^2$; the grammage of the fabric is approximately 45 g/m$^2$ (this fabric is manufactured by Texinov). The fabric is coated with a layer of gel by passing it through a bath of molten gel at 135–145° C. and the excess is removed by passing the fabric between two fixed rolls, the separation of which is predetermined depending on the result desired. Next, the compress in web form is cooled by an upflow of cold air. The amount of gel deposited on the yarns of the fabric is approximately 130 g/m$^2$. The cooled web is complexed with a polyester protective film 23 μm thick on each of its sides, and then it is cut into sheets in order to form compresses, each being packaged in a small bag sealed and sterilized under 9 radiation.

EXAMPLE 2

This example uses a fabric and a gel which are identical to Example 1, but the machines are adjusted so as to give a web comprising 60 g of gel per m$^2$.

EXAMPLE 3

A sterile compress is produced which is similar to Example 1, apart from the hydrocolloid which, instead of being sodium carboxymethylcellulose, is a propylene glycol alginate sold under the name PROTANAL ester SDLB by Pronova Biopolymer.

EXAMPLE 4

A compress is manufactured in a manner similar to Example 1, apart from the amounts of plasticizer which are 13.2 kg of ONDINA 15 paraffin oil (i.e. approximately 65% of the total mass of the gel) and 3.04 kg of Codex A vaseline (i.e. approximately 15% of the mass of the gel), respectively.

EXAMPLE 5

A compress is prepared in a manner similar to Example 1, apart from the elastomer which in this case is a mixture of 600 g of Kraton G 1651 and 400 g of Kraton G 1652.

EXAMPLE 6

The compress is prepared from a gel having a formulation similar to that described in Example 1, but the fabric used is a rectangular-mesh viscose gauze sold by Molypharm under the reference 548. The amount of gel deposited on the yarns of the fabric is approximately 180 g/m$^2$.

EXAMPLE 7

The compress is manufactured in a manner similar to Example 1, apart from the elastomer which in this case is a high-molecular-weight elastomer of the S-EP-S type having the reference SEPTON 4055, obtained from Kuraray. The amounts used are the same as in Example 1.

EXAMPLE 8

The compress is produced in a manner similar to Example 5, apart from the elastomeric gel to which, at the end of mixing, 200 g of silver sulfadiazine are added in the form of a finely divided powder. This active principle gives the compress antiseptic properties.

The healing power and the ease of use of the dressing compresses according to the invention were evaluated and compared with existing products commonly used for the protection and care of wounds. The study was carried out on dermo-epidermic wounds in guinea pigs.

In order to conduct these tests, a square dermoepidermic wound 9 cm$^2$ in area was made on the flank of each guinea pig (5 animals per group), leaving the platysma muscle in place. The sterile compresses to be studied were applied to the wound and covered with a sterile gauze and an adhesive tape. The dressing was renewed every two days at the start of treatment, and thereafter every three days. The progress of the healing was thus monitored for 22 days. The effectiveness of each of the compresses was evaluated by monitoring, according to a grid of pre-established criteria, the moisture content of the dressing, its adhesion to the wound, the inflammatory or hemorrhaging nature and the degree of healing of the wound.

The study was conducted comparatively on three examples produced according to the invention and two commercially available products. The results are as follows:

- with the compress according to Example 1 described above, one wound had completely healed after 22 days, three wounds had almost healed and the last wound had a small unhealed area (0.1 cm$^2$). No adhesion of the dressing was observed throughout the treatment, no inclusion was detected and the dressing dried out slightly;
- with the compress according to Example 2, one wound had completely healed after 19 days, three wounds had healed after 22 days and the last wound had a small unhealed area (0.5 cm$^2$). No adhesion of the dressing and no inclusion were observed throughout the duration of the treatment. The dressing remained quite wet at the start of treatment and dried out slightly by the end of the treatment;
- with the compress according to Example 6, no wound had healed after 22 days, one was very close to healing, the others had a small unhealed area (0.5 to 0.6 cm$^2$). In very rare cases, the dressing exhibited slight adhesion to the wound, but no inclusion was apparent. The dressing dried out slightly at all stages of the healing;
- the first comparative product was a commercial tulle gras dressing composed of a viscose fabric coated with vaseline and containing approximately 1% Peru balm (according to the description given in the 1998 Vidal dictionary), with which two wounds had healed after 22 days of treatment and the other three wounds were of modest size (0.6 to 1 cm$^2$). With this product, systematic adhesion to the wound was detected, especially during the first 15 days, as well as inclusions during the first 6 days. The dressing dried out substantially throughout the treatment;
- the second comparative product is a commercial compress formed from a viscose knit impregnated with an oil-in-water emulsion (according to the monograph appearing in the 1998 Vidal dictionary); with this interface, no wound had healed after 22 days, two were in the process of advanced healing (the residual wound had an area of 0.1 to 0.3 cm$^2$) and two were still large (approximately 1 cm$^2$). Quite frequent adhesion of the dressing was noted during the first 15 days, but there was very little inclusion. The dressing had a dry appearance throughout the treatment.

In the light of these various trials, it is apparent that the sterile compresses according to the invention, especially when they incorporate a fabric of hydrophobic synthetic fibers, allow wounds to heal more rapidly. In addition, because the dressings adhere neither to wounds nor to perilesional skin, they allow in all circumstances a change of dressing which is painless and much more comfortable for the patient.

What is claimed is:

1. A sterile nonstick compress, comprising an open-mesh flexible fabric, said fabric comprising yarns which are coated with a cohesive and nonstick gel so as to leave the meshes essentially unobstructed, wherein the yarns are continuous filaments of low extensibility and the gel is formed from a highly plasticized hydrophobic elastomeric matrix containing 1000 to 2000 parts of an oily plasticizer based on parafin oil and 0 to 400 parts of petrolum and a dispersion of hydrophillic particles of a hydrocolloid, said hydrocolloid being present in an amount of from 3 to 20% by weigt of said gel;
    wherein said hydrophobic elastomeric matrix comprises a high-molecular-weight triblock elastomer which is one of styrene-ethylene/butylene styrene, styrene-ethylene/propylene-styrene or mixtures thereof.

2. A dressing compress as claimed in claim 1, wherein the fabric is formed from nonelastic continuous multifilament yarns of low extensibility.

3. The compress as claimed in claim 1, wherein the yarns making up the fabric are of a hydrophobic nature.

4. The compress as claimed in claim 3, wherein the yarns making up the fabric are made of a polyester, and wherein said polyester is polyethylene terephthalate.

5. The compress as claimed in claim 1, wherein the hydrophobic elastomerc matrix
    wherein said high-molecular-weight triblock elastomer is plaaticized by means of a paraffin oil or a mixture of vaseline and paraffin oil.

6. The compress as claimed in claim 1, wherein the hydrocolloid is sodium carboxymethylcellulose.

7. The compress as claimed in claim 1, wherein the hydrocolloid is a propylene glycol alginate.

8. The compress as claimed in claim 1, wherein the gel furthermore contains an active principle.

9. The compress as claimed in claim 8, wherein the active principle is an antiseptic, an antibiotic or an anti-inflammatory.

10. A continuous process for manufacturing a compress according to claim 1, which consists in immersing a web of open-mesh fabric made of non-extensible yarns in a bath of molten gel, in passing it between two fixed rolls having a predetermined gap, in cooling said web, the yarns of which are covered with the gel, and in cutting, packaging and sterilizing the web in order to make individual compresses therefrom.

11. A sterile non-stick compress, comprising an open-mesh flexible fabric, said fabric comprising yarns which are coated with a cohesive and nonstick gel so as to leave the meshes essentially unobstructed, wherein the yarns are continuous filaments of low extensibility and the gel is formed from a highly plasticized hydrophobic elastomeric matrix containing 100 parts of a high-molecular-weight triblock elastomer per 1000 to 2000 parts of an oily plasticizer based on paraffin oil and 0 to 400 parts of petrolatum, and a dispersion of hydrophilic patricles of a hydrocolloid, said hydrocolloid being present in an amount of from 3 to 20% by weight of said gel, wherein said high-molecular-weight triblock elastomer is one of a copolymer of polystyrene blocks and poly-ethylene/butylene blocks, a copolymer of polystyrene blocks and poly-ethylene/prolylene blocks or a mixture thereof.

* * * * *

UNITED STATES PATENT AND TRADEMARK OFFICE
CERTIFICATE OF CORRECTION

PATENT NO.     : 6,270,792 B1
DATED          : August 7, 2001
INVENTOR(S)    : Guillemet, Alain et al.

It is certified that error appears in the above-identified patent and that said Letters Patent is hereby corrected as shown below:

<u>Title page,</u>
Item [73], Assignee: should read -- DIETETIQUE --

Signed and Sealed this

Thirteenth Day of August, 2002

*Attest:*

*Attesting Officer*

JAMES E. ROGAN
*Director of the United States Patent and Trademark Office*